United States Patent [19]

Blythin et al.

[11] Patent Number: 4,680,297

[45] Date of Patent: Jul. 14, 1987

[54] TRICYCLIC POSITIVE INOTROPIC AGENTS

[75] Inventors: David J. Blythin, N. Caldwell; Robert W. Watkins, Bloomfield, both of N.J.

[73] Assignee: Schering Corporation, Kenilworth, N.J.

[21] Appl. No.: 746,914

[22] Filed: Jun. 20, 1985

Related U.S. Application Data

[63] Continuation of Ser. No. 513,544, Jul. 14, 1983, abandoned.

[51] Int. Cl.$^4$ .................. A61K 31/50; A61K 31/495; A61K 31/44
[52] U.S. Cl. ..................................... 514/293; 514/291; 514/292; 514/250
[58] Field of Search .................. 546/83; 514/250, 291, 514/292, 293

[56] References Cited

U.S. PATENT DOCUMENTS 4,113,731  9/1978  Winters et al. ........................ 546/70
4,232,017  11/1980  Winters et al. ........................ 514/222
4,452,800  6/1984  Sherlock ............................. 514/300

OTHER PUBLICATIONS

Bulletin de la Societe Chimique de France, No. 1, 1968, pp. 364–369, Paris, FR; C. Fournier et al.
Chemical Abstracts, vol. 88, 1978, pp. 570–571, No. 105298y.
Journal of the Chemical Society, Perkin Transaction 1, Sep. 1983, pp. 2077–2087, London, GB; D. G. Hawkins et al.
Chemical Abstracts, vol. 101, No. 5, 30th Jul. 1984, p. 504, No. 38382t, E. M. Peresleni et al.
Japanese published patent 5-8-144-391 (abstract thereof).

Primary Examiner—Leonard Schenkman
Assistant Examiner—Joseph A. Lipovsky
Attorney, Agent, or Firm—James R. Nelson; Stephen I. Miller; Richard C. Billups

[57] ABSTRACT

Substituted quinoline, [1,5]- and [1,8]-naphthyridine and pyrido [2,3-b]pyrazine derivatives are useful positive inotropic agents.

21 Claims, No Drawings

TRICYCLIC POSITIVE INOTROPIC AGENTS

This is a continuation of application Ser. No. 513,544, filed July 14, 1983, now abandoned.

BACKGROUND OF THE INVENTION

The present invention relates to the use of certain tricyclic compounds for increasing cardiac contractility, i.e., they are positive inotropic agents.

SUMMARY OF THE INVENTION

The invention sought to be patented in its pharmaceutical method aspect is a method for increasing cardiac contractility in a mammal which method comprises the administration to said mammal of a compound having the structural formula I

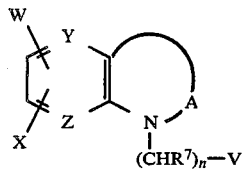

wherein:
A is

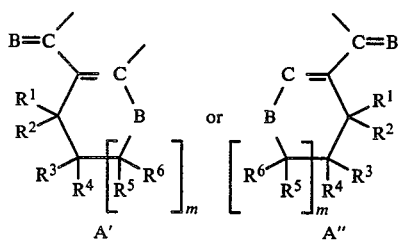

B is independently oxygen or sulfur;
$R^1$-$R^6$ may be the same or different and are hydrogen or alkyl having from 1 to 6 carbon atoms;
m is 0 or 1, provided that, when m is 0, $R^2$ and $R^4$ may be joined to form a carbon to carbon bond;
n is 0, 1 or 2;
W and X may be the same or different and are hydrogen, alkyl having from 1 to 6 carbon atoms, alkoxy having from 1 to 6 carbon atoms, halogen, trifluoromethyl, nitro, cyano, carboxy, hydroxy, alkenyloxy having from 3 to 8 carbon atoms, alkynyloxy having from 3 to 8 carbon atoms, cycloalkyl having from 4 to 8 carbon atoms, $S(O)_pR^a$ [wherein p is 0, 1 or 2 and $R^a$ is alkyl having from 1 to 6 carbon atoms], or phenoxy [wherein the benzene ring may be substituted with any of the other substituents W and X];
Y and Z may be the same or different and are CH or N;
V is phenyl, naphthyl, indenyl, indanyl, pyridyl, pyrimidinyl, thienyl, furyl or thiazolyl, any of which may be substituted with W and X as defined herein; and
$R^7$ is independently hydrogen or alkyl having from 1 to 6 carbon atoms.

A preferred method of the invention utilizes compounds having structural formula I wherein B is oxygen.

A more preferred method of the invention utilizes compounds having structural formula I wherein B is oxygen and A is A'.

A still more preferred method of the invention utilizes compounds having the structural formula:

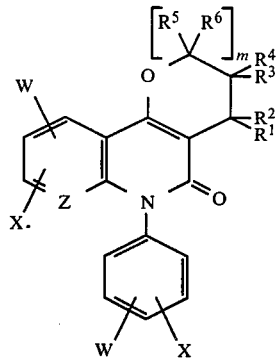

wherein W, X, Z, $R^1$-$R^6$ and m are as defined herein.

Preferred species having structural formula I for use in the method of the invention are those having the names:
3,5-dihyro-5-phenyl-furo[3,2-c][1,8]-naphthyridin-4[2H]-one;
6-phenyl-2,3,4,6-tetrahydro-pyrano[3,2-c][1,8]naphthyridin-5-one;
2-methyl-3,5-dihydro-5-phenyl-furo[3,2-c][1,8]naphthyridin-[4[2H]-one;
3,9-dihydro-9-phenyl-furo[2,3-b][1,8]naphthyridin-4[2H]-one;
3,9-dihydro-9-(p-methylphenyl)-furo[2,3-b][1,8]naphthyridin-4[2H]-one;
3,9-dihydro-2-methyl-9-phenyl-furo[2,3-b][1,8]naphthyridin-4[2H]-one;
3,5-dihydro-5-(p-methylphenyl)-furo[3,2-c][1,8]naphthyridin-4[2H]-one;
3,5-dihydro-5-(p-fluorophenyl)-furo[3,2-c][1,8]naphthyridin-4[2H]-one;
3,5-dihydro-5-(m-methoxyphenyl)-furo[3,2-c][1,8]naphthyridin-4[2H]-one;
3,5-dihydro-5-(m-methylthiophenyl)-furo[3,2-c][1,8]-naphthyridin-4[2H]-one;
3,9-dihydro-9-(p-fluorophenyl)-furo[2,3-b][1,8]naphthyridin-4[2H]-one;
3,9-dihydro-9-(m-methoxyphenyl)-furo[2,3-b][1,8]naphthyridin-4[2H]-one; and
3,9-dihydro-9-(m-methylthiophenyl)-furo[3,2-c][1,8]-naphthyridin-4[2H]-one.

The invention sought to be patented in its pharmaceutical composition aspect is a pharmaceutical composition useful for producing an increase in cardiac contractility in a mammal which comprises a compound having structural formula I in combination with a pharmaceutically acceptable carrier.

DESCRIPTION OF THE INVENTION

The compounds having structural formula I which are used in the method and compositions of the invention may be prepared from a properly substituted 3-(hydroxyalkyl)-4-hydroxy-1-substituted-[quinolin; 1,5-naphthyridin; or 1,8-naphthyridin]-2(1H)-one, a 7-(hydroxyalkyl)-8-hydroxy-5-substituted-pyrido[2,3-b]-pyrazin-6(5H)-one or a sulfur derivative thereof having the structural formula II

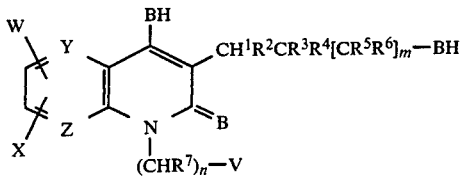

wherein B, V, W, X, Y, Z, $R^1$-$R^7$, n and m are as defined herein.

The compounds having structural formula I wherein A is A', i.e., compounds having structural formula I'

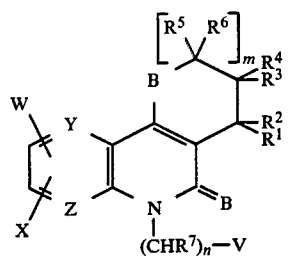

may be prepared by treating a correspondingly substituted compound having structural formula II with a strong aqueous acid solution. Useful acids are sulfuric acid, hydrobromic acid, perchloric acid, trifluoroacetic acid, phosphoric acid and the like. A compatible non-reactive solvent may be utilized to aid solubility, if desired. The use of approximately 30% sulfuric acid without additional solvent is preferred.

In this procedure, the starting compound II is dissolved or suspended in the reaction medium and heated to reflux temperature over a period of about 1 hour. The mixture is maintained at reflux temperature until the reaction is substantially complete. The progress of the reaction may be monitored by standard means, for example thin layer chromatographic means, and is usually substantially completed after about 6 hours. The product may be recovered, for example, by adding the reaction mixture to an excess of cold dilute base solution such as sodium hydroxide, potassium carbonate or the like and isolating the product by standard means such as extraction with an organic solvent or by filtration. Further purification, if desired, may be effected by recrystallization.

The compounds having structural formula I wherein A is A", i.e., compounds having structural formula I"

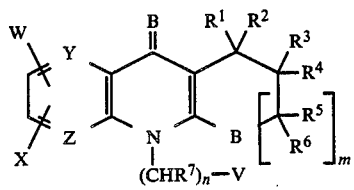

may be prepared by treating a corresponding substituted compound having structural formula II with a dehydrating reagent under anhydrous conditions. Suitable dehydrating reagents for this purpose are phosphorus pentoxide/methanesulfonic acid [known as Eaton's reagent, J. Org. Chem., -35, 4071 (1973)]and thionyl chloride/pyridine/methylene chloride, for example.

In the preferred method for preparing compounds having structural formula I", a correspondingly substituted compound having structural formula II is dissolved or suspended in Eaton's reagent at elevated temperature until the reaction is substantially complete. Temperatures from about 50° to 100° C. are useful. At temperatures of from about 60° to 80° C., the reaction has been observed to be substantially completed in about 1 to about 4 hours.

The progress of the reaction may be monitored by standard means. The product may be recovered, for example, by adding the reaction mixture to an excess of cold dilute base solution such as sodium hydroxide, potassium carbonate or the like and isolating the product by standard means such as extraction with an organic solvent or by filtration. Further purification, if desired, may be effected by recrystallization.

The compounds having structural formula II may be prepared by known methods from known starting materials. Exemplary of such starting materials are 2-anilino nicotinic acids prepared, for example, as described in U.S. Pat. No. Re. 26,655, and 2-phenylamino-3-pyrazine carboxylate esters which may be prepared substantially as exemplified herein starting with a 2-amino-3-pyrazine carboxylate ester. 2-Anilino-3-pyrazine carboxylic acid is a known compound, C.A., 75, 20154e (1971), which may be esterified by standard procedures.

The compounds having structural formula I' may also be produced from a correspondingly substituted compound having structural formula I". Thus for example, a compound having structural formula I" may be treated with a nucleophile such as bromide or iodide anion under anhydrous conditions in a non-reactive solvent such as N,N-dimethylacetamide between about 60° C. and the mixture's reflux temperature for about 2 to about 12 hours to effect this conversion.

Certain compounds having structural formula I in which one or both of B are sulfur may be prepared from the correspondingly substituted compound having structural formula II by treatment with, for example, Lawesson's Reagent [2,4-bis(4-methoxyphenyl)-1, 3-dithia-2,4-diphosphetane-2,4-disulfide]in hot toluene. Under these conditions both cyclization of II and thiation are found to occur. Also, reaction of Lawesson's Reagent with compounds I' wherein both B substituents are oxygen yields mainly a singly thiated product, i.e. the product in which =BH is sulfur (a thioamide); whereas —B— is not replaced and remains oxygen.

In addition, certain compounds wherein one of the B substituents is oxygen and one is sulfur may be rearranged by treatment with a nucleophile as described above. Thus, for example, a thioamide compound wherein the cyclic B atom is oxygen having structural formula I', may be rearranged to produce a compound having structural formula I" wherein the cyclic B atom is sulfur and the doubly bonded B atom is oxygen.

When utilized herein and in the appended claims the below listed terms, unless specified otherwise, are defined as follows:

halogen—fluorine, chlorine, bromine and iodine;
alkyl and alkoxy—comprised of straight and branched carbon chains containing from 1 to 6 carbon atoms;
alkenyloxy—comprised of straight and branched carbon chains containing from 3 to 8 carbon atoms and comprising a carbon to carbon double bond; and alkynyloxy—comprised of straight and branched carbon chains containing from 3 to 8 carbon atoms and comprising a carbon to carbon triple bond.

The compounds having structural formula I may possibly contain two different "B" substituents. It is intended that both may simultaneously be oxygen or sulfur, or that either may be oxygen or sulfur.

The compounds having structural formula I are comprised of a $-(CHR^7)_n-$ substituent wherein the $R^7$ group may vary independently. Thus, for example, when n equals 2 the following patterns of substitution (wherein $CH_3$ is used to represent any substituent, $R^7$,) are contemplated: $-CH_2CH(CH_3)-$, $CH(CH_3)CH_2-$, $-(C(CH_3)H)_2-$ and the like. In addition when n equals 2, substituents such as $-CH(CH_3)CH(C_2H_5)-$, $-CH(i-C_3H_7)CH(C_2H_5)-$ are also contemplated.

Certain compounds having structural formula I may exist in isomeric forms. The invention contemplates all such isomers both in pure form and in admixture, including racemic mixtures.

The compounds having structural formula I have been found to increase cardiac contractility. As such, these compounds are useful in the treatment of congestive heart failure.

Selected compounds having structural formula I were tested for their ability to increase cardiac contractility both in vitro and in vivo.

In vitro tests were conducted on left atria obtained from guinea pigs employing the method described in Am. J. Physiology 221:1470–1475 (1971). Increases in cardiac contractility were found at concentrations ranging from 1 μgm/ml to 1000 μgm/ml with increases in cardiac contractility found generally from 10 μgm/ml to 100 μgm/ml.

In vivo tests were conducted on conscious, chronically instrumented dogs employing methods similar to those described in Circ. Res. 45, 666–667 (1980). Increases in cardiac contractility were generally found at dosage levels of 1 mg/kg to 10 mg/kg, upon oral administration.

The compounds having structural formula I can exist in unsolvated as well as solvated forms, including hydrated forms. In general, the solvated forms, with pharmaceutically acceptable solvents such as water, ethanol and the like are equivalent to the unsolvated forms for purposes of the invention.

For preparing pharmaceutical compositions from the compounds having structural formula I, inert, pharmaceutically acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The invention also contemplates the use of mechanical delivery systems such as transdermal delivery systems.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to 100 mg according to the particular application and the potency of the active ingredient. The compositions can, if desired, also contain other therapeutic agents.

The dosages may be varied depending upon the requirements of the patient, the severity of the condition being treated and the particular compound being employed. Typically, a daily dosage regimen would generally be from about 1 mg/kg to about 10 mg/kg administered orally, and from about 0.1 mg/kg to about 10 mg/kg when administered parenterally. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

EXAMPLES

EXAMPLE 1

3,9-Dihydro-9-(4-methylphenyl)-furo[2,3-b][1,8]-naphthyridin-4(2H)-one

A solution of 4-hydroxy-3-(2-hydroxyethyl)-1-(4-methylphenyl)-1,8-naphthyridin-2(1H)-one (2.2 g.) in Eaton's Reagent (10% $P_2O_5$ in methane sulfonic acid; 40 ml.) was stirred in an atmosphere of nitrogen and heated to 70° C. for 2 hr. After cooling, the product was poured into water, adjusted to pH 4 with NaHCO$_3$, filtered, washed with water, air dried and was recrystallized from isopropanol with decolorization to yield the product, m.p. 246–248.5° C.

EXAMPLE 2

9-(3,4-Dichlorophenyl)-3,9-dihydro-2-methyl-furo-[2,3-b][1,8]naphthyridin-4(2H)-one A solution of 1-(3,4-dichlorophenyl)-4-hydroxy-3-(2-hydroxypropyl)-1,8-naphthyridin-2(1H)-one (5 g.) in Eaton's Reagent (10% $P_2O_5$ in methanesulfonic acid; 100 ml.), under an atmosphere of nitrogen, was heated at 70° C. for 2 hr. The mixture was cooled and poured into water. The pH was adjusted to 7 with NaHCO$_3$. The product was filtered off, washed with water, dried in air, and recrystallized from isopropanol/charcoal to yield the product, m.p. 218–220.5° C.

The following compounds may be similarly prepared by substituting the appropriate starting material and using the method of Example 1 or 2.

3,9-Dihydro-9-phenyl-furo[2,3-b][1,8]-naphthyridin-4(2H)-one
3,9-Dihydro-2-methyl-9-phenyl-furo[2,3-b][1,8]-naphthyridin-4(2H)-one
3,9-Dihydro-2-(n-butyl)-9-phenyl-furo[2,3-b]-[1,8]naphthyridin-4(2H)-one
3,9-Dihydro-9-(4-fluorophenyl)-furo[2,3-b]-[1,8]naphthyridin-4(2H)-one
3,9-Dihydro-2-methyl-9-(4-fluorophenyl)-furo[2,3-b][1,8]naphthyridin-4(2H)-one
3,9-Dihydro-2-(n-butyl)-9-(4-fluorophenyl)furo[2,3-b][1,8]naphthyridin-4(2H)-one
3,9-Dihydro-9-(4-chlorophenyl)-furo[2,3-b][1,8]-naphthyridin-4(2H)-one
3,9-Dihydro-2-methyl-9-(4-chlorophenyl)-furo [2,3-b]1,8]naphthyridin-4(2H)-one
3,9-Dihydro-9-(4-methoxyphenyl)-furo[2,3-b][1,8]naphthyridin-4(2H)-one
3,9-Dihydro-2-methyl-9-(4-methoxyphenyl)-furo[2,3-b][1,8]naphthyridin-4(2H)-one
3,9-Dihydro-9-(3-methoxyphenyl)-furo[2,3-b][1,8]naphthyridin-4(2H)-one
3,9-Dihydro-2-methyl-9-(3-methoxyphenyl)-furo[2,3-b][1,8]naphthyridin-4(2H)-one
3,9-Dihydro-9-(3-methylmercaptophenyl)-furo[2,3-b][1,8]naphthyridin-4(2H)-one
3,9-Dihydro-2-methyl-9-(3-methylmercaptophenyl)-furo[2,3-b][1,8]naphthyridin-4(2H)-one
3,9-Dihydro-9-benzyl-furo[2,3-b][1,8]naphthyridin-4(2H)-one
3,9-Dihydro-2-methyl-9-benzyl-furo[2,3-b][1,8]-naphthyridin-4(2H)-one
3,9-Dihydro-9-(2-phenylethyl)-furo[2,3-b][1,8]-naphthyridin-4(2H)-one
3,9-Dihydro-2-methyl-9-(2-phenylethyl)-furo[2,3-b][1,8]naphthyridin-4(2H)-one
3,9-Dihydro-9-(2-thienylmethyl)-furo[2,3-b][1,8]naphthyridin-4(2H)-one
3,9-Dihydro-9-(2-thiazolyl)-furo[2,3-b][1,8]naphthyridin-4(2H)-one
3,9-Dihydro-9-(2-pyridyl)-furo[2,3-b][1,8]naphthyridin-4(2H)-one
3,9-Dihydro-9-[2-(2-pyridyl)ethyl]-furo[2,3-b][1,8]naphthyridin-4(2H)-one
3,9-Dihydro-9-(3-chlorophenyl)-furo[2,3-b][1,8]naphthyridin-4(2H)-one
3,9-Dihydro-9-(3,5-dichlorophenyl)-furo[2,3-b][1,8]naphthyridin-4(2H)-one
3,9-Dihydro-2-methyl-9-(3,5-dichlorophenyl)furo[2,3-b][1,8]naphthyridin-4(2H)-one
3,9-Dihydro-9-(2,3-dichlorophenyl)-furo[2,3-b][1,8]naphthyridin-4(2H)-one
3,9-Dihydro-2-methyl-9-(2,3-dichlorophenyl)furo[2,3-b][1,8]naphthyridin-4(2H)-one
3,9-Dihydro-9-(2,5-dichlorophenyl)-furo[2,3-b][1,8]naphthyridin-4(2H)-one
3,9-Dihydro-9-(3-chloro-4-fluorophenyl)-furo[2,3-b][1,8]naphthyridin-4(2H)-one
3,9-Dihydro-2-methyl-9-(3-chloro-4-fluorophenyl)-furo[2,3-b][1,8]naphthyridin-4(2H)-one
3,9-Dihydro-9-(3-trifluoromethylphenyl)-furo[2,3-b][1,8]naphthyridin-4(2H)-one
3,9-Dihydro-2-methyl-9-(3-trifluoromethylphenyl)-furo[2,3-b][1,8]naphthyridin-4(2H)-one
3,9-Dihydro-9-phenyl-furo[2,3-b]quinolin-4(2H)-one
3,9-Dihydro-2-methyl-9-phenyl-furo[2,3-b]quinolin-4(2H)-one
3,9-Dihydro-2-(n-butyl)-9-phenyl-furo[2,3-b]quinolin-4(2H)-one
3,9-Dihydro-9-(4-fluorophenyl)-furo[2,3-b]quinolin-4(2H)-one
3,9-Dihydro-2-methyl-9-(4-fluorophenyl)-furo[2,3-b]quinolin-4(2H)-one
3,9-Dihydro-2-(n-butyl)-9-(4-fluorophenyl)furo[2,3-b]quinolin-4(2H)-one
3,9-Dihydro-9-(4-chlorophenyl)-furo[2,3-b]quinolin-4(2H)-one
3,9-Dihydro-2-methyl-9-(4-chlorophenyl)-furo[2,3-b]quinolin-4(2H)-one
3,9-Dihydro-9-(3-methoxyphenyl)-furo[2,3-b]quinolin-4(2H)-one
3,9-Dihydro-2-methyl-9-(3-methoxyphenyl)-furo[2,3-b]quinolin-4(2H)-one 3,9-Dihydro-9-(3-methylmercaptophenyl)-furo[2,3-b]quinolin-4(2H)-one
3,9-Dihydro-2-methyl-9-(3-methylmercaptophenyl)-furo[2,3-b]quinolin-4(2H)-one
3,9-Dihydro-9-benzyl-furo[2,3-b]quinolin-4(2H)-one
3,9-Dihydro-2-methyl-9-benzyl-furo[2,3-b]quinolin-4(2H)-one
3,9-Dihydro-9-(2-phenylethyl)-furo[2,3-b]quinolin-4(2H)-one
3,9-Dihydro-2-methyl-9-(2-phenylethyl)-furo[2,3-b]quinolin-4(2H)-one
3,9-Dihydro-9-(2-thienylmethyl)-furo[2,3-b]quinolin-4(2H)-one
3,9-Dihydro-9-(2-thiazolyl)-furo[2,3-b]quinolin-4(2H)-one
3,9-Dihydro-9-(2-pyridyl)-furo[2,3-b]quinolin-4(2H)-one
3,9-Dihydro-9-[2-(2-pyridyl)ethyl]-furo[2,3-b]quinolin-4(2H)-one
3,9-Dihydro-9-(3-chlorophenyl)-furo[2,3-b]quinolin-4(2H)-one
3,9-Dihydro-2-methyl-9-(3-chlorophenyl)-furo[2,3-b]quinolin-4(2H)-one
2,3,4,10-Tetrahydro-10-phenyl-pyrano[2,3-b][1,8]naphthyridin-5-one
2,3,4,10-Tetrahydro-2-methyl-10-phenyl-pyano[2,3-b][1,8]naphthyridin-5-one
2,3,4,10-Tetrahydro-10-(4-fluorophenyl)-pyrano[2,3-b][1,8]naphthyridin-5-one
2,3,4,10-Tetrahydro-10-(4-chlorophenyl)-pyrano[2,3-b][1,8]naphthyridin-5-one
2,3,4,10-Tetrahydro-10-(3,4-dichlorophenyl)-pyrano[2,3-b][1,8]naphthyridin-5-one
2,3,4,10-Tetrahydro-10-(4-methylphenyl)-pyrano[2,3-b][1,8]naphthyridin-5-one
2,3,4,10-Tetrahydro-10-(4-methoxyphenyl)-pyrano[2,3-b][1,8]naphthyridin-5-one
2,3,4,10-Tetrahydro-10-(3-methoxyphenyl)-pyrano[2,3-b][1,8]naphthyridin-5-one
2,3,4,10-Tetrahydro-10-(3-methylmercaptophenyl)-pyrano[2,3-b][1,8]naphthyridin-5-one
2,3,4,10-Tetrahydro-10-benzyl-pyrano[2,3-b][1,8]naphthyridin-5-one
2,3,4,10-Tetrahydro-10-(2-phenylethyl)-pyrano[2,3-b][1,8]naphthyridin-5-one
2,3,4,10-Tetrahydro-10-(2-thienylmethyl)-pyrano[2,3-b][1,8]naphthyridin-5-one
2,3,4,10-Tetrahydro-10-(2-thiazolyl)-pyrano[2,3-b][1,8]naphthyridin-5-one
2,3,4,10-Tetrahydro-10-[2-(2-pyridyl)ethyl]pyrano[2,3-b][1,8]naphthyridin-5-one
2,3,4,10-Tetrahydro-10-(3-chlorophenyl)-pyrano[2,3-b][1,8]naphthyridin-5-one
2,3,4,10-Tetrahydro-10-phenyl-pyrano[2,3-b]quinoline-5-one
2,3,4,10-Tetrahydro-2-methyl-10-phenyl-pyrano[2,3-b]quinoline-5-one
2,3,4,10-Tetrahydro-6-chloro-10-phenyl-pyrano[2,3-b]quinoline-5-one
2,3,4,10-Tetrahydro-6-fluoro-10-phenyl-pyrano[2,3-b]quinoline-5-one
2,3,4,10-Tetrahydro-6-methoxy-10-phenyl-pyrano[2,3-b]quinoline-5-one
2,3,4,10-Tetrahydro-6-methyl-10-phenyl-pyrano[2,3-b]quinoline-5-one
2,3,4,10-Tetrahydro-7-chloro-10-phenyl-pyrano[2,3-b]quinoline-5-one
2,3,4,10-Tetrahydro-7-fluoro-10-phenyl-pyrano[2,3-b]quinoline-5-one
2,3,4,10-Tetrahydro-7-methoxy-10-phenyl-pyrano[2,3-b]quinoline-5-one
2,3,4,10-Tetrahydro-10-(4-fluorophenyl)-pyrano[2,3-b]quinoline-5-one
2,3,4,10-Tetrahydro-10-(4-chlorophenyl)-pyrano[2,3-b]quinoline-5-one
2,3,4,10-Tetrahydro-10-(4-methoxyphenyl)-pyrano[2,3-b]quinoline-5-one
2,3,4,10-Tetrahydro-10-(3-methoxyphenyl)-pyrano[2,3-b]quinoline-5-one
2,3,4,10-Tetrahydro-10-(3-methylmercaptophenyl)-pyrano[2,3-b]quinoline-5-one
2,3,4,10-Tetrahydro-10-benzyl-pyrano[2,3-b]quinoline-5-one
2,3,4,10-Tetrahydro-10-(2-phenylethyl)-pyrano[2,3-b]quinoline-5-one
2,3,4,10-Tetrahydro-10-(2-thienylmethyl)-pyrano[2,3-b]quinoline-5-one
2,3,4,10-Tetrahydro-10-(2-thiazolyl)-pyrano[2,3-b]quinoline-5-one
2,3,4,10-Tetrahydro-10-[2-(2-pyridyl)ethyl]pyrano[2,3-b]quinoline-5-one
2,3,4,10-Tetrahydro-10-(3-chlorophenyl)-pyrano[2,3-b]quinoline-5-one
3,9-Dihydro-9-phenyl-furo[2,3-b][1,5]naphthyridin-4-(2H)-one
3,9-Dihydro-2-methyl-9-phenyl-furo[2,3-b][1,5]naphthyridin-4-(2H)-one
3,9-Dihydro-2-(n-butyl)-9-phenyl-furo[2,3-b][1,5]naphthyridin-4-(2H)-one
3,9-Dihydro-9-(4-fluorophenyl)-furo[2,3-b][1,5]naphthyridin-4-(2H)-one
3,9-Dihydro-2-methyl-9-(4-fluorophenyl)-furo[2,3-b][1,5]naphthyridin-4-(2H)-one
3,9-Dihydro-9-(4-chlorophenyl)--furo[2,3-b][1,5]naphthyridin-4-(2H)-one
3,9-Dihydro-9-(4-methoxyphenyl)-furo[2,3-b][1,5]naphthyridin-4-(2H)-one
3,9-Dihydro-9-(4-methylphenyl)-furo[2,3-b][1,5]naphthyridin-4-(2H)-one
3,9-Dihydro-9-(3,4-dichlorophenyl)-furo[2,3-b][1,5]naphthyridin-4-(2H)-one
3,9-Dihydro-9-(3-methoxyphenyl)-furo[2,3-b][1,5]naphthyridin-4-(2H)-one
3,9-Dihydro-9-(3-methylmercaptophenyl)-furo[2,3-b][1,5]naphthyridin-4-(2H)-one
3,9-Dihydro-9-(3-chlorophenyl)-furo[2,3-b][1,5]naphthyridin-4-(2H)-one
3,9-Dihydro-9-benzyl-furo[2,3-b][1,5]naphthyridin-4-(2H)-one
3,9-Dihydro-9-(2-thienylmethyl)-furo[2,3-b][1,5]naphthyridin-4-(2H)-one
3,9-Dihydro-9-(2-thiazolyl)-furo[2,3-b][1,5]naphthyridin-4-(2H)-one
2,3,4,10-Tetrahydro-10-phenyl-pyrano[2,3-b][1,5]naphthyridin-5-one
2,3,4,10-Tetrahydro-2-methyl-10-phenyl-pyrano[2,3-b][1,5]naphthyridin-5-one
2,3,4,10-Tetrahydro-10-(4-fluorophenyl)-pyrano[2,3-b][1,5]naphthyridin-5-one
2,3,4,10-Tetrahydro-10-(4-chlorophenyl)-pyrano[2,3-b][1,5]naphthyridin-5-one
2,3,4,10-Tetrahydro-10-(3-methoxyphenyl)-pyrano[2,3-b][1,5]naphthyridin-5-one
2,3,4,10-Tetrahydro-10-(3-methylmercaptophenyl)-pyrano[2,3-b][1,5]naphthyridin-5-one 2,3,4,10-Tetrahydro-10-(3-chlorophenyl)-pyrano[2,3-b][1,5]naphthyridin-5-one
2,3,4,10-Tetrahydro-10-benzyl-pyrano[2,3-b][1,5]naphthyridin-5-one
2,3,4,10-Tetrahydro-10-(2-thienylmethyl)-pyrano[2,3-b][1,5]naphthyridin-5-one
7,8-Dihydro-5-phenyl-furo[3', 2':5,6]pyrido[2,3-b]pyrazin-9(5H)-one
7,8-Dihydro-2-methyl-5-phenyl-furo[3', 2':5,6]pyrido[2,3-b]pyrazin-9(5H)-one
7,8-Dihydro-2-(n-butyl)-5-phenyl-furo[3',2':5,6]pyrido[2,3-b]pyrazin-9(5H)-one
7,8-Dihydro-2,3-dimethyl-5-phenyl-furo[3',2':5,6]pyrido[2,3-b]pyrazin-9(5H)-one
7,8-Dihydro-2,3,7-trimethyl-5-phenyl-furo[3',2':5,6]pyrido[2,3-b]pyrazin-9(5H)-one
7,8-Dihydro-5-(4-fluorophenyl)-furo[3',2':5,6-]pyrido[2,3-b]pyrazin-9(5H)-one
7,8-Dihydro-2-methyl-5-(4-fluorophenyl)-furo [3',2':5,6]pyrido[2,3-b]pyrazin-9(5H)-one
7,8-Dihydro-2,3-dimethyl-5-(4-fluorophenyl)-furo[3',2':5,6]pyrido[2,3-b]pyrazin-9(5H)-one
7,8-Dihydro-2,3,7-trimethyl-5-(4-fluorophenyl) furo[3',2:5,6]pyrido[2,3-b]pyrazin-9(5H)-one
7,8-Dihydro-5-(4-chlorophenyl)-furo[3',2':5,6 ]pyrido[2,3-b]pyrazin-9(5H)-one
7,8-Dihydro-5-(4-methylphenyl)-furo[3',2':5,6-]pyrido[2,3-b]pyrazin-9(5H)-one
7,8-Dihydro-5-(4-methoxyphenyl)-furo[3',2':5,6-]pyrido[2,3-b]pyrazin-9(5H)-one
7,8-Dihydro-5-(3-methoxyphenyl)-furo[3',2':5,6-]pyrido[2,3-b]pyrazin-9(5H)-one
7,8-Dihydro-5-(3-methylmercaptophenyl)-furo[3',2'5,6]pyrido[2,3-b]pyrazin-9(5H)-one
7,8-Dihydro-5-(3-chlorophenyl)-furo[3',2':5,6-]pyrido[2,3-b]pyrazin-9(5H)-one
5,7,8,9-Tetrahydro-5-phenyl-10H-pyrano-[3',2':5,6]pyrido[2,3,-b]pyrazin-10-one
5,7,8,9-Tetrahydro-7-methyl-5-phenyl-10H-pyrano[3',2':5,6]pyrido[2,3-b]pyrazin-10-one
5,7,8,9-Tetrahydro-5-(4-fluorophenyl)-10H-pyrano[3',2':5,6]pyrido[2,3-b]pyrazin-10-one
5,7,8,9-Tetrahydro-2,3-dimethyl-5-(4-fluorophenyl)-10H-pyrano[3',2':5,6]pyrido[2,3-b]pyrazin10-one
5,7,8,9-Tetrahydro-7-methyl-5-(4-fluorophenyl)-10H-pyrano[3',2':5,6]pyrido[2,3-b]pyrazin-10-one
5,7,8,9-Tetrahydro-5-(3-methoxyphenyl)-10H-pyrano[3',2':5,6]pyrido[2,3-b]pyrazin-10-one
5,7,8,9-Tetrahydro-5-(3-methylmercaptophenyl)-10H-pyrano[3',2':5,6]pyrido[2,3-b]pyrazin-10-one
5,7,8,9-Tetrahydro-5-(3-chlorophenyl)-10H-pyrano[3',2':5,6]pyrido[2,3-b]pyrazin-10-one
5,7,8,9-Tetrahydro-7-methyl-5-(3-methoxyphenyl)-10H-pyrano[3',2':5,6]pyrido[2,3-b]pyrazin-10-one
5,7,8,9-Tetrahydro-7-methyl-5-(3-chlorophenyl)-10H-pyrano[3',2':5,6]pyrido[2,3-b]pyrazin-10-one

EXAMPLE 3

3,9-Dihydro-2-methyl-9-phenyl-furo[2,3-b][1,8]naphthyridin-4(2H)-one

A suspension of 4-hydroxy-3-(2-hydroxypropyl)1-phenyl-1,8-naphthyridin-2(1H)-one (1 g.) in $CH_2Cl_2$ was stirred in an atmosphere of nitrogen. To this was added pyridine (1.5 ml.). To this mixture was added a solution of $SOCl_2$ (1.5 ml.) in $CH_2Cl_2$ (10 ml.) dropwise over a period of 15 minutes. The mixture was stirred overnight at room temperature then water was added. The $CH_2Cl_2$ layer was separated, dried and evaporated. Recrystallization from isopropanol yielded the product, m.p. 207°–209° C.

EXAMPLE 4

5-(3,4-Dichlorophenyl)-3,5-dihydro-2-methyl-furo [3,2-c][1,8]naphthyridin-4(2H)-one A solution of p-toluene sulfonic acid (5g.) in toluene (100 ml.) was prepared. To this was added 1-(3,4-dichlorophenyl)-4-hydroxy-3-(2-hydroxypropyl)1,8-naphthyridin-2(1H)-one (5g.) and the mixture was stirred and heated to reflux in an atmosphere of nitrogen. The mixture was refluxed for 18 hrs. The resulting solution was poured into water (200 ml.), stirred for ½ hr. then filtered. The solids were recrystallized from isopropanol to yield the product, m.p. 273°–274° C.

EXAMPLE 5

2-n-Butyl-3,5-dihydro-5-phenyl-furo [3,2-c][1,8]naphthyridin-4(2H)-one

A solution of 4-hydroxy-3-(2-hydroxyhexyl)-1-phenyl-1,8-naphthyridin-2(1H)-one (2g.) in 47% HBr was stirred in an atmosphere of nitrogen and heated to 80° C. for 4½ hrs. after which time it was cooled and poured into water. The precipitate was filtered off, washed with water, dried in air, recrystallized from ethanol/charcoal to yield the product m.p. 179°–180° C.

EXAMPLE 6

2-Methyl-3,5-dihydro-5-phenyl-furo[3,2-c][1,8]naphthyridin-4(2H)-one.

A solution of 4-hydroxy-3-(2-hydroxypropyl)-1-phenyl-1,8-naphthyridin-2(1H)-one (8.9 g; 0.03 mole) in 47% HBr (90 ml.) was stirred in an atmosphere of nitrogen. The solution was heated to 90° C. for 4½ hrs. then was allowed to cool, poured into water and was adjusted to pH 4.5 with sodium acetate. The product was filtered off, washed with water, dried in air and recrystallized from $CHCl_3$/isopropanol to yield the product, m.p. 223°–224° C.

EXAMPLE 7

6-Phenyl-2,3,4,6-tetrahydro-pyrano[3,2-c][1,8]naphthyridin-5-one

A suspension of 4-hydroxy-3-(3-hydroxypropyl)1-phenyl-1,8-naphthyridin-2(1H)-one (5.67 g.) in 47% HBr (50 ml.) was stirred in an atmosphere of nitrogen and was heated to 90° C. for 5 hrs. After cooling, the product was poured into water, and the pH was adjusted to 4.5 with potassium acetate. Chromatographic purification of the product on silica gel eluting with $CH_2Cl_2$: 5% ether and subsequent recrystallization of the product from the relevant fractions yielded the product, m.p. 253°–255° C.

EXAMPLE 8

3,5-Dihydro-5-phenyl-furo[3,2-c][1,8] naphthyridin-4(2H)-one

A solution of 4-hydroxy-3-(2-hydroxyethyl)1-phenyl-1,8-naphthyridin-2-(1H)-one (10 g.) in 30% (v/v) sulfuric acid (200 ml.) was heated to reflux, in an atmosphere of nitrogen, and was held at reflux until no further reaction occured (ca. 5–8 hrs.). After cooling, the solution was added slowly and carefully to an icecooled solution of sodium hydroxide (50% solution; 200 ml.). The mixture was allowed to stand overnight and was then filtered. The product was washed with water, dried in air and recrystallized from dimethylformamide/water, with charcoal treatment, to yield the product, m.p. 276°–277.5° C.

The following compounds may be similarly prepared by substituting the appropriate starting material and using the method of Examples 5, 6, 7 or 8.

3,5-Dihydro-5-(4-chlorophenyl)-furo[3,2-c][1,8]naphthyridin-4(2H)-one
3,5-Dihydro-2-methyl-5-(4-chlorophenyl)-furo[3,2-c][1,8]naphthyridin-4(2H)-one
3,5-Dihydro-2-ethyl-5-(4-chlorophenyl)-furo[3,2-c][1,8]naphthyridin-4(2H)-one
3,5-Dihydro-2-(n-propyl)-5-(4-chlorophenyl)furo[3,2-c][1,8]naphthyridin-4(2H)-one
3,5-Dihydro-2-(n-butyl)-5-(4-chlorophenyl)furo[3,2-c][1,8]naphthyridin-4(2H)-one
3,5-Dihydro-2-ethyl-5-phenyl-furo[3,2-c][1,8]naphthyridin-4(2H)-one
3,5-Dihydro-2-(n-propyl)-5-phenyl-furo[3,2-c][1,8]naphthyridin-4(2H)-one
3,5-Dihydro-2-(iso-butyl)-5-phenyl-furo[3,2-c][1,8]naphthyridin-4(2H)-one
3,5-Dihydro-2,2-dimethyl-5-phenyl-furo[3,2-c][1,8]naphthyridin-4(2H)-one
3,5-Dihydro-5-(4-fluorophenyl)-furo[3,2-c][1,8]naphthyridin-4(2H)-one
3,5-Dihydro-2-methyl-5-(4-fluorophenyl)-furo[3,2-c][1,8]naphthyridin-4(2H)-one
3,5-Dihydro-2-ethyl-5-(4-fluorophenyl)-furo[3,2-c][1,8]naphthyridin-4(2H)-one
3,5-Dihydro-2-(n-propyl)-5-(4-fluorophenyl)furo[3,2-c][1,8]naphthyridin-4(2H)-one
3,5-Dihydro-2-(n-butyl)-5-(4-fluorophenyl)-furo[3,2-c][1,8]naphthyridin-4(2H)-one
3,5-Dihydro-5-(4-methylphenyl)-furo[3,2-c][1,8]naphthyridin-4(2H)-one
3,5-Dihydro-2-methyl-5-(4-methylphenyl)furo[3,2-c][1,8]naphthyridin-4(2H)-one
3,5-Dihydro-2-(n-butyl)-5-(4-methylphenyl)furo[3,2-c][1,8]naphthyridin-4(2H)-one
3,5-Dihydro-5-(4-methoxyphenyl)-furo[3,2-c][1,8]naphthyridin-4(2H)-one
3,5-Dihydro-2-methyl-5-(4-methoxyphenyl)-furo[3,2-c][1,8]naphthyridin-4(2H)-one
3,5-Dihydro-2-(n-butyl)-5-(4-methoxyphenyl)furo[3,2-c][1,8]naphthyridin-4(2H)-one
3,5-Dihydro-5-(3,4-dichlorophenyl)-furo[3,2-c][1,8]naphthyridin-4(2H)-one
3,5-Dihydro-2-methyl-5-(3,4-dichlorophenyl)furo[3,2-c][1,8]naphthyridin-4(2H)-one
3,5-Dihydro-2-(n-butyl)-5-(3,4-dichlorophenyl)-furo[3,2-c][1,8]naphthyridin-4(2H)-one
3,5-Dihydro-5-(3-methoxyphenyl)-furo[3,2-c][1,8]naphthyridin-4(2H)-one
3,5-Dihydro-2-methyl-5-(3-methoxyphenyl)-furo[3,2-c][1,8]naphthyridin-4(2H)-one
3,5-Dihydro-2-(n-butyl)-5-(3-methoxyphenyl)-furo[3,2-c][1,8]naphthyridin-4(2H)-one
3,5-Dihydro-5-(3-methylmercaptophenyl)-furo[3,2-c][1,8]naphthyridin-4(2H)-one
3,5-Dihydro-2-methyl-5-(3-methylmercaptophenyl)-furo[3,2-c][1,8]naphthyridin-4(2H)-one
3,5-Dihydro-2-(n-butyl)-5-(3-methylmercaptophenyl)-furo[3,2-c][1,8]naphthyridin-4(2H)-one
3,5-Dihydro-5-(3-methylsulfinylphenyl)-furo[3,2-c][1,8]naphthyridin-4(2H)-one
3,5-Dihydro-2-methyl-5-(3-methylsulfinylphenyl)-furo[3,2-c][1,8]naphthyridin-4(2H)-one
3,5-Dihydro-2-(n-butyl)-5-(3-methylsulfinylphenyl)-furo[3,2-c][1,8]naphthyridin-4(2H)-one
3,5-Dihydro-5-(3-methylsulfonylphenyl)-furo[3,2-c][1,8]naphthyridin-4(2H)-one
3,5-Dihydro-2-methyl-5-(3-methylsulfonylphenyl)-furo-[3,2-c][1,8]naphthyridin-4(2H)-one
3,5-Dihydro-2-(n-butyl)-5-(3-methylsulfonylphenyl)-furo[3,2-c][1,8]naphthyridin-4(2H)-one
3,5-Dihydro-5-(3,5-dichlorophenyl)-furo[3,2-c][1,8]naphthyridin-4(2H)-one
3,5-Dihydro-2-methyl-5-(3,5-dichlorophenyl-furo3,2-c][1,8]naphthyridin-4(2e,uns/H/ )-one
3,5-Dihydro-5-(2,3-dichlorophenyl-furo[3,2-c][1,8]naphthyridin-4(2H)-one
3,5-Dihydro-2-methyl-5-(2,3-dichlorophenyl)-furo[3,2-c][1,8]naphthyridin-4(2H)-one
3,5-Dihydro-5-(2,5-dichlorophenyl)-furo[3,2-c][1,8]naphthyridin-4(2H)-one
3,5-Dihydro-2-methyl-5-(2,5-dichlorophenyl)-furo[3,2-c][1,8]naphthyridin-4(2H)-one
3,5-Dihydro-5-(3-chloro-4-fluorophenyl)-furo[3,2-c][1,8]naphthyridin-4(2H)-one
3,5-Dihydro-2-methyl-5-(3-chloro-4-fluorophenyl)-furo[3,2-c][1,8]naphthyridin-4(2H)-one
3,5-Dihydro-2-methyl-5-(3-trifluoromethylphenyl)-furo[3,2-c][1,8]naphthyridin-4(2H)-one
3,5-Dihydro-2-methyl-5-(3-trifluoromethylphenyl)-furo[3,2-c][1,8]naphthyridin-4(2H)-one
3,5-Dihydro-5-(3-chlorophenyl)-furo[3,2-c][1,8]naphthyridin-4(2H)-one
3,5-Dihydro-2-methyl-5-(3-chlorophenyl)-furo [1,8]naphthyridin-4(2H)-one
3,5-Dihydro-5-benzyl-furo[3,2-c][1,8]naphthyridin-4(2H)-one
3,5-Dihydro-2-methyl-5-benzyl-furo[3,2-c][1,8]naphthyridin-4(2H)-one
3,5-Dihydro-5-(2-phenylethyl)-furo[3,2-c][1,8]naphthyridin-4(2H)-one
3,5-Dihydro-2-methyl-5-(2-phenylethyl)-furo[3,2-c][1,8]naphthyridin-4(2H)-one
3,5-Dihydro-5-(1-phenylethyl)-furo[3,2-c][1,8]naphthyridin-4(2H)-one
3,5-Dihydro-2-methyl-5-(1-phenylethyl)-furo[3,2-c][1,8]naphthyridin-4(2H)-one
3,5-Dihydro-5-(2-thienylmethyl)-furo[3,2-c][1,8]naphthyridin-4(2H)-one
3,5-Dihydro-2-methyl-5-(2-thienylmethyl)-furo[3,2-c][1,8]naphthyridin-4(2H)-one
3,5-Dihydro-5-(2-thiazolyl)-furo[3,2-c][1,8]naphthyridin-4(2H)-one
3,5-Dihydro-2-methyl-5-(2-thiazolyl)-furo[3,2-c][1,8]naphthyridin-4(2H)-one
3,5-Dihydro-5-(2-pyridyl)-furo[3,2-c][1,8]naphthyridin-4(2H)-one
3,5-Dihydro-5-[2-(2-pyridyl)ethyl]-furo[3,2-c][1,8]naphthyridin-4(2H)-one
3,5-Dihydro-5-phenyl-furo[3,2-c]quinolin-4(2H)-one
3,5-Dihydro-2-methyl-5-phenyl-furo[3,2-c]quinolin-4(2H)-one
3,5-Dihydro-2-(n-butyl)-5-phenyl-furo[3,2-c]quinolin-4(2H)-one
3,5-Dihydro-8-chloro-5-phenyl-furo[3,2-c]quinolin-4(2H)-one
3,5-Dihydro-2-methyl-8-chloro-5-phenyl-furo[3,2-c]quinolin-4(2H)-one 3,5-Dihydro-8-fluoro-5-phenyl-furo[3,2-c]quinolin-4(2H)-one
3,5-Dihydro-2-methyl-8-fluoro-5-phenyl-furo[3,2-c]quinolin-4(2H)-one
3,5-Dihydro-8-methoxy-5-phenyl-furo[3,2-c]quinolin-4(2H)-one
3,5-Dihydro-2-methyl-8-methoxy-5-phenyl-furo[3,2-c]quinolin-4(2H)-one
3,5-Dihydro-7-chloro-5-phenyl-furo[3,2-c]quinolin-4(2H)-one
3,5-Dihydro-2-methyl-7-chloro-5-phenyl-furo[3,2-c]quinolin-4(2H)-one
3,5-Dihydro-7-fluoro-5-phenyl-furo[3,2-c]quinolin-4(2H)-one
3,5-Dihydro-2-methyl-7-fluoro-5-phenyl-furo[3,2-c]quinolin-4(2H)-one
3,5-Dihydro-5-(4-fluorophenyl)-furo[3,2-c]quinolin-4(2H)-one
3,5-Dihydro-2-methyl-5-(4-fluorophenyl)-furo[3,2-c]quinolin-4(2H)-one F
3,5-Dihydro-5-(3-methoxyphenyl)-furo[3,2-c]quinolin-4(2H)-one
3,5-Dihydro-2-methyl-5-(3-methoxyphenyl)-furo[3,2-c]quinolin-4(2H)-one
3,5-Dihydro-5-(3-methylmercaptophenyl)-furo[3,2-c]quinolin-4(2H)-one
3,5-Dihydro-2-methyl-5-(3-methylmercaptophenyl)-furo[3,2-c]quinolin-4(2H)-one
3,5-Dihydro-5-(3,5-dichlorophenyl)-furo[3,2-c]quinolin-4(2H)-one
3,5-Dihydro-2-methyl-5-(3,5-dichlorophenyl)-furo[3,2-c]quinolin-4(2H)-one
3,5-Dihydro-2-methyl-5-(3-chlorophenyl)-furo[3,2-c]quinolin-4(2H)-one
3,5-Dihydro-5-(3-chlorophenyl)-furo[3,2-c]quinolin-4(2H)-one
3,5-Dihydro-5-(3-trifluoromethylphenyl)-furo[3,2-c]quinolin-4(2H)-one
3,5-Dihydro-2-methyl-5-(3-trifluoromethylphenyl)-furo[3,2-c]quinolin-4(2H)-one
3,5-Dihydro-5-(3-chloro-4-fluorophenyl)-furo[3,2-c]quinolin-4(2H)-one
3,5-Dihydro-2-methyl-5-(3-chloro-4-fluorophenyl)-furo[3,2-c]quinolin-4(2H)-one
3,5-Dihydro-5-benzyl-furo[3,2-c]quinolin-4(2H)-one
3,5-Dihydro-2-methyl-5-benzyl-furo[3,2-c]quinolin-4(2H)-one
3,5-Dihydro-5-(2-phenylethyl)-furo[3,2-c]quinolin-4(2H)-one
3,5-Dihydro-5-(2-thienylmethyl)-furo[3,2-c]quinolin-4(2H)-one
3,5-Dihydro-5-(2-pyridyl)-furo[3,2-c]quinolin-4(2H)-one
3,5-Dihydro-[2-(2-pyridyl)ethyl]-5-furo[3,2-c]quinolin-4(2H)-one
2,3,4,6-Tetrahydro-6-phenyl-pyrano[3,2-c][1,8]naphthyridin-5-one
2,3,4,6-Tetrahydro-2-methyl-6-phenyl-pyrano[3,2-c][1,8]naphthyridin-5-one
2,3,4,6-Tetrahydro-6 -(4-fluorophenyl)-pyrano[3,2-c][1,8]naphthyridin-5-one
2,3,4,6-Tetrahydro-6-(4-chlorophenyl)-pyrano[3,2-c][1,8]naphthyridin-5-one
2,3,4,6-Tetrahydro-6-(3,4-dichlorophenyl)-pyrano[3,2-c][1,8]naphthyridin-5-one
2,3,4,6-Tetrahydro-6-(4-methylphenyl)-pyrano[3,2-c][1,8]naphthyridin-5-one
2,3,4,6-Tetrahydro-6-(4-methoxyphenyl)-pyrano[3,2-c][1,8]naphthyridin-5-one
2,3,4,6-Tetrahydro-6-(3-methoxyphenyl)-pyrano[3,2-c][1,8]naphthyridin-5-one
2,3,4,6-Tetrahydro-6-(3-chlorophenyl)-pyrano[3,2-c][1,8]naphthyridin-5-one
2,3,4,6-Tetrahydro-6-(3-methylmercaptophenyl)-pyrano[3,2-c][1,8]naphthyridin-5-one
2,3,4,6-Tetrahydro-6-(3,5-dichlorophenyl)-pyrano[3,2-c][1,8]naphthyridin-5-one
2,3,4,6-Tetrahydro-6-(2,3-dichlorophenyl)-pyrano [3,2-c][1,8]naphthyridin-5-one
2,3,4,6-Tetrahydro-6-(2,5-dichlorophenyl)-pyrano [3,2-c][1,8]naphthyridin-5-one
2,3,4,6-Tetrahydro-6-(3-chloro-4-fluorophenyl)-pyrano[3,2-c][1,8]naphthyridin-5-one
2,3,4,6-Tetrahydro-6-(3-trifluoromethylphenyl)-pyrano[3,2-c][1,8]naphthyridin-5-one
2,3,4,6-Tetrahydro-6-benzyl-pyrano-[3,2-c][1,8]naphthyridin-5-one
2,3,4,6-Tetrahydro-6-(2-phenylethyl)-pyrano[3,2-c][1,8]naphthyridin-5-one
2,3,4,6-Tetrahydro-6-(2-thienylmethyl)-pyrano[3,2-c][1,8]naphthyridin-5-one
2,3,4,6-Tetrahydro-6-(2-thiazolyl)-pyrano[3,2-c][1,8]naphthyridin-5-one
2,3,4,6-Tetrahydro-6-(2-[2-pyridyl]ethyl-pyrano[3,2-c][1,8]naphthyridin-5-one
2,3,4,6-Tetrahydro-6-phenyl-pyrano[3,2-c]quinolin-5-one
2,3,4,6-Tetrahydro-2-methyl-6-phenyl-pyrano[3,2-c]quinolin-5-one
2,3,4,6-Tetrahydro-9-chloro-6-phenyl-pyrano[3,2-c]quinolin-5-one
2,3,4,6-Tetrahydro-9-fluoro-6-phenyl-pyrano[3,2-c]quinolin-5-one
2,3,4,6-Tetrahydro-9-methoxy-6-phenyl-pyrano[3,2-c]quinolin-5-one
2,3,4,6-Tetrahydro-9-methyl-6-phenyl-pyrano[3,2-c]quinolin-5-one
2,3,4,6-Tetrahydro-8-chloro-6-phenyl-pyrano[3,2-c]quinolin-5-one
2,3,4,6-Tetrahydro-8-fluoro-6-phenyl-pyrano[3,2-c]quinolin-5-one
2,3,4,6-Tetrahydro-8-methoxy-6-phenyl-pyrano[3,2-c]quinolin-5-one
2,3,4,6-Tetrahydro-6-(4-fluorophenyl)-pyrano[3,2-c]quinolin-5-one
2,3,4,6-Tetrahydro-6-(4-chlorophenyl)-pyrano[3,2-c]quinolin-5-one
2,3,4,6-Tetrahydro-6-(4-methoxyphenyl)-pyrano[3,2-c]quinolin-5-one
2,3,4,6-Tetrahydro-6-(3-chlorophenyl)-pyrano[3,2-c]quinolin-5-one
2,3,4,6-Tetrahydro-6-(3-methoxyphenyl)-pyrano[3,2-c]quinolin-5-one
2,3,4,6-Tetrahydro-6-(3-methylmercaptophenyl)-pyrano[3,2-c]quinolin-5-one
2,3,4,6-Tetrahydro-6-benzyl-pyrano-[3,2-c]quinolin-5-one
2,3,4,6-Tetrahydro-6-(2-phenylethyl)-pyrano[3,2-c]quinolin-5-one
2,3,4,6-Tetrahydro-6-(2-thienylmethyl)-pyrano[3,2-c]quinolin-5-one
2,3,4,6-Tetrahydro-6-(2-thiazolyl)-pyrano[3,2-c]quinolin-5-one
2,3,4,6-Tetrahydro-6-[2-(2-pyridyl)ethyl]-pyrano[3,2-c]quinolin-5-one 3,5-Dihydro-5-phenyl-furo[3,2-c][1,5]naphthyridin-4(2H)-one
3,5-Dihydro-2-methyl-5-phenyl-furo[3,2-c][1,5]naphthyridin-4(2H)-one
3,5-Dihydro-2-ethyl-5-phenyl-furo[3,2-c][1,5]naphthyridin-4(2H)-one
3,5-Dihydro-2-(n-butyl)-5-phenyl-furo[3,2-c][1,5]naphthyridin-4(2H)-one
3,5-Dihydro-5-(4-chlorophenyl)-furo[3,2-c][1,5]naphthyridin-4(2H)-one
3,5-Dihydro-2-methyl-5-(4-chlorophenyl)-furo[3,2-c][1,5]naphthyridin-4(2H)-one
3,5-Dihydro-5-(4-fluorophenyl)-furo[3,2-c][1,5]naphthyridin-4(2H)-one
3,5-Dihydro-2-methyl-5-(4-fluorophenyl)-furo[3,2-c][1,5]naphthyridin-4(2H)-one
3,5-Dihydro-5-(4-methylphenyl)-furo[3,2-c][1,5]naphthyridin-4(2H)-one
3,5-Dihydro-5-(4-methoxyphenyl)-furo[3,2-c][1,5]naphthyridin-4(2H)-one
3,5-Dihydro-5-(3,4-dichlorophenyl)-furo[3,2-c][1,5]naphthyridin-4(2H)-one
3,5-Dihydro-5-(3-methoxyphenyl)-furo[3,2-c][1,5]naphthyridin-4(2H)-one
3,5-Dihydro-2-methyl-5-(3-methoxyphenyl)-furo[3,2-c][1,5]naphthyridin-4(2H)-one
3,5-Dihydro-5-(3-methylmercaptophenyl)-furo[3,2-c][1,5]naphthyridin-4(2H)-one
3,5-Dihydro-2-methyl-5-(3-methylmercaptophenyl)-furo[3,2-c][1,5]naphthyridin-4(2H)-one
3,5-Dihydro-5-(3-chlorophenyl)-furo[3,2-c][1,5]naphthyridin-4(2Hone
3,5-Dihydro-2-methyl-5-(3-chlorophenyl)-furo[3,2-c][1,5]naphthyridin-4(2H)-one
3,5-Dihydro-5-benzyl-furo[3,2-c][1,5]naphthyridin-4(2H)-one
3,5-Dihydro-5-(2-thienylmethyl)-furo[3,2-c][1,5]naphthyridin-4(2H)-one
3,5-Dihydro-5-(2-thiazolyl)-furo[3,2-c][1,5]naphthyridin-4(2H)-one
3,5-Dihydro-5-(2-pyridyl)-furo[3,2-c][1,5]naphthyridin-4(2H)-one
3,5-Dihydro-5-[2-(2-pyridyl)ethyl]-furo[3,2-c][1,5]naphthyridin-4(2H)-one
2,3,4,6-Tetrahydro-6-phenyl-pyrano[3,2-c][1,5]naphthyridin-5-one
2,3,4,6-Tetrahydro-2-methyl-6-phenyl-pyrano[3,2-c][1,5]naphthyridin-5-one
2,3,4,6-Tetrahydro-6-(4-fluorophenyl)-pyrano[3,2-c][1,5]naphthyridin-5-one
2,3,4,6-Tetrahydro-6-(4-chlorophenyl)-pyrano[3,2-c][1,5]naphthyridin-5-one
2,3,4,6-Tetrahydro-6-(3,4-dichlorophenyl)-pyrano[3,2-c][1,5]naphthyridin-5-one
2,3,4,6-Tetrahydro-6-(4-methylphenyl)-pyrano[3,2-c][1,5]naphthyridin-5-one
2,3,4,6-Tetrahydro-6-(4-methoxyphenyl)-pyrano[3,2-c][1,5]naphthyridin-5-one
2,3,4,6-Tetrahydro-6-(3-methoxyphenyl)-pyrano[3,2-c][1,5]naphthyridin-5-one
2,3,4,6-Tetrahydro-6-(3-methylmercaptophenyl)-pyrano[3,2-c][1,5]naphthyridin-5-one
2,3,4,6-Tetrahydro-6-(3-chlorophenyl)-pyrano[3,2-c][1,5]naphthyridin-5-one
2,3,4,6-Tetrahydro-6-benzyl-pyrano-[3,2-c][1,5]naphthyridin-5-one
2,3,4,6-Tetrahydro-6-(2-phenylethyl)-pyrano[3,2-c][1,5]naphthyridin-5-one
2,3,4,6-Tetrahydro-6-(2-thienylmethyl)-pyrano[3,2-c][1,5]naphthyridin-5-one
2,3,4,6-Tetrahydro-6-(2-thiazolyl)-pyrano[3,2-c][1,5]naphthyridin-5-one
2,3,4,6-Tetrahydro-6-(2-[2-pyridyl]ethyl)-pyrano[3,2-c][1,5]naphthyridin-5-one
7,8-Dihydro-5-phenyl-furo[2',3':4,5]pyrido[2,3-b]pyrazin-6(5H)-one
7,8-Dihydro-8-methyl-5-phenyl-furo[2',3':4,5]pyrido 2,3-b]pyrazin-6(5H)-one
7,8-Dihydro-8-(n-butyl)-5-phenyl-furo[2',3':4,5-]pyrido[2,3-b]pyrazin-6(5H)-one
7,8-Dihydro-5-(4-fluorophenyl)-furo[2',3':4,5-]pyrido[2,3-b]pyrazin-6(5H)-one
7,8-Dihydro-8-methyl-5-(4-fluorophenyl)-furo2',3':4,5-]pyrido[2,3-b]pyrazin-6(5H)-one
7,8-Dihydro-2,3-dimethyl-5-(4-fluorophenyl)-furo[2',3':4,5]pyrido[2,3-b]pyrazin-6(5H)-one
7,8-Dihydro-2,3,8-trimethyl-5-(4-fluorophenyl)-furo[2',3':4,5]pyrido[2,3-b]pyrazin-6(5H)-one
7,8-Dihydro-5-(4-chlorophenyl)-furo[2',3':4,5-]pyrido[2,3-b]pyrazin-6(5H)-one
7,8-Dihydro-5-(4-methylphenyl)-furo[2',3':4,5-]pyrido[2,3-b]pyrazin-6(5H)-one
7,8-Dihydro-5-(4-methoxyphenyl)-furo[2',3':4,5-]pyrido[2,3-b]pyrazin-6(5H)-one
7,8-Dihydro-5-(3-methoxyphenyl)-furo[2',3':4,5-]pyrido[2,3-b]pyrazin-6(5H)-one
7,8-Dihydro-8-methyl-5-(3-methoxyphenyl)-furo[2',3':4,5]pyrido[2,3-b]pyrazin-6(5H)-one
7,8-Dihydro-2,3-dimethyl-5-(3-methoxyphenyl)-furo[2',3':4,5]pyrido[2,3-b]pyrazin-6(5H)-one
7,8-Dihydro-5-(3-methylmercaptophenyl)-furo[2',3':4,5]pyrido[2,3-b]pyrazin-6(5H)-one
7,8-Dihydro-8-methyl-5-(3-methylmercaptophenyl)-furo[2',3':4,5]pyrido[2,3-b]pyrazin-6(5H)-one
7,8-Dihydro-2,3-dimethyl-5-(3-methylmercaptophenyl)-furo[2',3':4,5]pyrido[2,3-b]pyrazin-6(5H)-one
7,8-Dihydro-5-(3-chlorophenyl)-furo-[2',3':4,5]pyrido[2,3-b]pyrazin-6(5H)-one
7,8-Dihydro-8-methyl-5-(3-chlorophenyl)-furo[2',3':4,5]pyrido[2,3-b]pyrazin-6(5H)-one
7,8-Dihydro-2,3-dimethyl-5-(3-chlorophenyl)-furo-[2',3':4,5]pyrido[2,3-b]pyrazin-6(5H)-one
5,7,8,9-Tetrahydro-5-phenyl-6H-pyrano[2',3':4,5-]pyrido[2,3-b]pyrazin-6-one
5,7,8,9-Tetrahydro-9-methyl-5-phenyl-6H-pyrano[2',3':4,5]pyrido[2,3-b]pyrazin-6-one
5,7,8,9-Tetrahydro-5-(4-fluorophenyl)-6H-pyrano[2',3':4,5]pyrido[2,3-b]pyrazin-6-one
5,7,8,9-Tetrahydro-2,3-dimethyl-5-(4-fluorophenyl)-6H-pyrano-[2',3':4,5]pyrido[2,3-b]pyrazin-one
5,7,8,9-Tetrahydro-5-(4-chlorophenyl)-6H-pyrano[2',3':4,5]pyrido[2,3-b]pyrazin-6-one
5,7,8,9-Tetrahydro-5-(4-methylphenyl)-6H-pyrano[2',3':4,5]pyrido[2,3-b]pyrazin-6-one
5,7,8,9-Tetrahydro-5-(4-methoxyphenyl)-6Hpyrano[2',3':4,5]pyrido[2,3-b]pyrazin-6-one
5,7,8,9-Tetrahydro-5-(3-methoxyphenyl)-6H-pyrano[2',3':4,5]pyrido[2,3-b]pyrazin-6-one
5,7,8,9-Tetrahydro-2,3-dimethyl-5-(4-fluorophenyl)-6H-pyrano[2',3':4,5]pyrido[2,3-b]pyrazin-6-one
5,7,8,9-Tetrahydro-5-(3-methylmercaptophenyl)-6H-pyrano[2',3':4,5]pyrido[2,3-b]pyrazin-6-one
5,7,8,9-Tetrahydro-2,3-dimethyl-5-(4-fluorophenyl)-6H-pyrano[2',3':4,5]pyrido[2,3-b]pyrazin-6-one
5,7,8,9-Tetrahydro-5-(3-chlorophenyl)-6H-pyrano[2',3':4,5]pyrido[2,3-b]pyrazin-6-one 5,7,8,9-Tetrahydro-2,3-dimethyl-5-(3-chlorophenyl)-6H-pyrano[2',3':4,5]pyrido[2,3-b]pyrazin-6-one

Example 9

5-(3,4-Dichlorophenyl)-3,5-dihydro-2-methyl-furo[3,2-c][1,8]naphthyridin-4(2H)-one To a solution of 9-(3,4-dichlorophenyl)-3,9-dihydro-2-methyl-furo[2,3-b][1,8]naphthyridin-4(2H)-one (125 mg.) (prepared as in example 2) in dimethylacetamide (20 ml.) in an atmosphere of nitrogen was added sodium iodide (250 mg.). The solution was refluxed for 4 hrs., and it was poured over ice-water, filtered, dried and recrystallized from isopropanol to yield the desired product, m.p. 273°-274° C.

Example 10

A mixture of 4-hydroxy-3-(2'-hydroxyethyl) 1-phenyl-1,8-naphthyridin-2(1H)-one (3 g.) and 2,4-bis (4-methoxyphenyl)-1,3-dithia-2,4-diphosphetane-2,4-disulfide (also known as Lawesson's Reagent) (4.3 g.) in toluene (100 ml) was stirred in an atmosphere of nitrogen and heated to reflux. The mixture was refluxed for 20 hr. after which it was cooled, evaporated, dissolved in $CH_2Cl_2$, washed with water, dried, and chromatographed over silica gel, eluting with increasing concentrations of ethyl acetate (0–5%) in $CH_2Cl_2$. Three products were isolated and characterised as follows:

1st compound eluted:
3,5-Dihydro-5-phenyl-thieno[3,2-c][1,8]naphthyridin-4[2H]-thione, m.p. 275°-276.5° C.

2nd compound eluted:
3,5-Dihydro-5-phenyl-furo[3,2-c][1,8]naphthyridin-4[2H]-thione, m.p. 243°-245.5° C.

3rd compound eluted:
3,9-Dihydro-9-phenyl-thieno[2,3-b][1,8]naphthyridin-4[2H]-thione, m.p. 264°-266° C. (dec)

In a similar manner, application of this procedure to other compounds having structural formula II would lead to the preparation of analogous products to those described in this Example.

Example 11

3,5-Dihydro-5-(4-methoxyphenyl)-furo[3,2-c][1,8]naphthyridin-4(2)-one

A solution of 3,9-dihydro-9-(4-methoxyphenyl)-furo[2,3-b][1,8]naphthyridin-4(2H)-one (1 g.) and sodium iodide (1 g.) in dry dimethylacetamide (10 ml.) was heated to 70° C. for 4 hr in a nitrogen atmosphere. The product was cooled, poured over ice-water, filtered, dried and recrystallized from $CH_2Cl_2$ to yield the desired product, m.p. 282°-284° C.

Essentially any of the products prepared according to the procedures of Examples 1 and 2 may be converted by this process into the products which may otherwise be prepared according to the procedures of Examples 5, 6, 7 and 8.

Example 12

3,5-Dihydro-5-phenyl-furo[3,2-c][1,8]naphthyridine-4(2H)-thione

A suspension of 3,5-dihydro-5-phenyl-furo[3,2-c][1,8]naphthyridin-4(2H)-one (3 g.) and 2,4-bis(4-methoxyphenyl)-1,3-dithia-2,4-diphosphetane-2,4-disulfide (Lawesson's Reagent; 5 g.) in dry toluene (100 ml.) was stirred in an atmosphere of nitrogen and heated to reflux for 6 hrs. After cooling, the organic layer was washed with water, dried and evaporated. The product was purified by chromatography over silica gel in $CH_2Cl_2$ containing increasing amounts of ethyl acetate (0–5%). The fractions containing pure product were combined, evaporated, suspended in ethanol, filtered and dried to yield the desired product, m.p. 242°-244.5° C.

In a similar manner, other compounds produced according to Examples 5, 6, 7 or 8 may be converted to their thione analogs by this process.

Example 13

3,9-Dihydro-9-phenyl-thieno[2,3-b][1,8]naphthyridin-4(2H)-one

A solution of 3,5-dihydro-5-phenyl-furo-[3,2-c][1,8]naphthyridin-4(2H)-thione (500 mg.) and sodium iodide (500 mg.) in dry dimethylacetamide (5 ml.) was stirred in an atmosphere of nitrogen and heated at 125° for 2 hr. After cooling, the solution was poured into ice-water, filtered, washed with water and dried to yield the desired product, m.p. 260°-261° C.

Similarly may be prepared other such derivatives from the corresponding starting materials prepared according to the method of Example 12.

Example 14

5-Phenyl-furo[3,2-c][1,8]naphthyridin-4[5H]-one

A mixture of 3,5-dihydro-5-phenyl-furo-[3,2-c][1,8]-naphthyridin-4[2H]-one (2 g.) and 2,3-dichloro-5,6-dicyano-1,4-benzoquinone (DDQ; 2 g.) in dry toluene (50 ml.) was stirred in an atmosphere of nitrogen and heated to reflux. Refluxing was continued for 20 hrs. After cooling somewhat the mixture was evaporated, dissolved in $CH_2Cl_2$, filtered and chromatographed on silica gel eluting with increasing concentrations of ethyl acetate in $CH_2Cl_2$ (0–10%). Evaporation of the relevant fractions and recrystallization from acetonitrile yielded the desired product, m.p. 245°-247° C.

In a similar manner, any of the tricyclicdihydro-furo derivatives may be oxidized to the corresponding furo-derivative.

Example 15

3,9-Dihydro-9-phenyl-furo[2,3-b][1,8]naphthyridin-4(2H)-thone

To a stirred suspension of 3,9-dihydro-9-phenyl-furo[2,3-b][1,8]naphthyridin-4(2H)-one(1 g.) in dry toluene (40 ml.) at 55° C., under an atmosphere of dry nitrogen, was added a suspension of 2,4-bis,(4-methoxyphenyl)-1,3-dithia-2,4-diphosphetane-2,4-disulfide (Lawesson'Reagent; 0.8 g) in dry toluene (10 ml.). The reaction was followed by t.l.c. (silica gel/$CH_2Cl_2$:5% Methanol) and warming was continued until no starting material remained (ca. 2½ hr.). Toluene was removed under reduced pressure and the product was dissolved in $CH_2Cl_2$. The solution was separated by chromatography on silica gel eluting with increasing concentrations of ethyl acetate in $CH_2Cl_{12}$ (2%–5%). The desired product was obtained as an orange-yellow solid, m.p. ca. 273°-275° C. (dec.).

Similarly, application of this procedure to other compounds having structural formula I'', prepared according to the procedures of Examples 1 or 2, will produce the thione analogs of compounds described in those examples.

Example 16

3,5-Dihyrdo-5-phenyl-thieno[3,2-c][1,8]naphthyridin-4(2H)-one

A solution of 3,5-dihydro-9-phenyl-furo-[2,3-b][1,8]-naphthyridin-4[2H]-thione (500 mg.) and sodium iodide (500 mg.) in dry dimethylacetamide (5 ml.) is stirred in an atmosphere of nitrogen and heated to 100° C. for 2 hrs. After cooling, the solution is poured into ice water, filtered, washed with water and dried to yield the desired product.

In a similar manner may be prepared other such derivatives from the corresponding starting materials prepared according to the method of Example 15.

Examples of such compounds are:
3,5-Dihydro-2-methyl-5-phenyl-thieno[3,2-c][1,8]naphthyridin-4(2H)-one
3,5-Dihydro-5-(4-fluorophenyl)-thieno[3,2-c][1,8]naphthyridin-4(2H)-one
3,5-Dihydro-2-methyl-5-(fluorophenyl)-thieno[3,2-c][1,8]naphthyridin-4(2H)-one
3,5-Dihydro-5-3-chlorophenyl)-thieno[3,2-c][1,8]naphthyridin-4(2H)-one
3,5-Dihydro-2-methyl-5-(3-chlorophenyl)-thieno[3,2-c][1,8]naphthyridin-4(2H)-one
3,5-Dihydro-5-(3-methoxyphenyl)-thieno[3,2-c][1,8]naphthyridin-4(2H)-one
3,5-Dihydro-2-methyl-5-(3-methoxyphenyl)-thieno[3,2-c][1,8]naphthyridin-4(2H)-one
3,5-Dihydro-5-(3-methylthiophenyl)-thieno[3,2-c][1,8]naphthyridin-4(2H)-one
3,5-Dihydro-2-methyl-5-(3-methylthiophenyl)-thieno[3,2-c][1,8]naphthyridin-4(2H)-one
3,5-Dihydro-5-(3-trifluoromethylphenyl)-thieno[3,2-c][1,8]naphthyridin-4(2H)-one
3,5-Dihydro-2-methyl-5-(3-trifluoromethylphenyl)-thieno[3,2-c][1,8]naphthyridin-4(2H)-one
3,5-Dihydro-5-(3,5-dichlorophenyl)-thieno[3,2-c][1,8]naphthyridin-4(2H)-one
3,5-Dihydro-2-methyl-5-(3,5-dichlorophenyl)-thieno[3,2-c][1,8]naphthyridin-4(2H)-one
3,5-Dihydro-5-(3-chloro-4-fluorophenyl)-thieno[3,2-c][1,8]naphthyridin-4(2H)-one
3,5-Dihydro-2-methyl-5-(3-chloro-4-fluorophenyl)-thieno[3,2-c][1,8]naphthyridin-4(2H)-one
3,5-Dihydro-5-(4-chlorophenyl)-thieno[3,2-c][1,8]naphthyridin-4(2H)-one
3,5-Dihydro-5-(4-methylphenyl)-thieno[3,2-c][1,8]naphthyridin-4(2H)-one
3,5-Dihydro-5-(4-methoxyphenyl)-thieno[3,2-c][1,8]naphthyridin-4(2H)-one
3,5-Dihydro-5-(3,4-dichlorophenyl)-thieno[3,2-c][1,8]naphthyridin-4(2H)-one
3,5-Dihydro-5-(3-methylsulfinylphenyl)-thieno[3,2-c][1,8]naphthyridin-4(2H)-one
3,5-Dihydro-5-(3-methylsulfonylphenyl)-thieno[3,2-c][1,8]naphthyridin-4(2H)-one

PREPARATIVE EXAMPLES

Preparative Example 1

3-(2-Hydroxyethyl)-4-hydroxy-1-phenyl-1,8-naphthyridin-2(1H)one

To a solution of 6.8 g. of methyl 2-phenylamino-3-pyridine carboxylate in 60 ml. of gamma-butyrolactone there was added, under nitrogen, 13.4 g. of potassium tertiary butoxide. The reaction mixture was heated and stirred for one hour at 95° C., poured on ice and stirred overnight. The mixture was extracted with ether, the aqueous layer acidified with acetic acid to pH 4.5 and the product was collected by filtration. Recrystallization from chloroform, acetone, isopropanol yielded the product of this example as a colorless solid; m.p. 235°–236° C.

According to this procedure, or an art-recognized modification thereof, any of the 2-hydroxyethyl sidechain materials used as starting materials in the reactions described in Examples 1-8 may be prepared.

Preparative Example 2

Methyl-2-phenylamino-3-pyrazine carboxylate (A) Methyl 2-bromo-3-pyrazine carboxylate:

To a stirred mixture of 12.7 g. of methyl 2-amino pyrazine carboxylate and 47 ml. of 48% hydrobromic acid there was added, dropwise, 12.6 ml. of bromine keeping the temperature at 0°. A solution of 14.4 g. of sodium nitrite in 60 ml. of water was then added, dropwise, at 0° and the reaction mixture stirred for 15 minutes. The reaction mixture was basified to pH 8 with sodium bicarbonate and extracted with ethyl acetate and again with chloroform. The organic layers were dried over magnesium sulfate, filtered and concentrated to a yellow oil. Recrystallization from ether-hexane yielded the product, m.p. 43°–45° C.

(B) Methyl 2-phenylamino-3-pyrazine carboxylate:

A mixture of 9.5 g. of methyl 2-bromo-3-pyrazine carboxylate, 8.2 g. of aniline, 0.5 g. of p-toluene sulfonic acid and 100 ml. of water was stirred and refluxed for two hours. The reaction mixture was poured on ice, extracted with ethyl acetate, the organic extracts were dried and concentrated to yield an oil. The crude residue was eluted on a silica gel column with ethyl acetate-hexane (1:2) yielding the product of this example as a yellow solid, m.p. 72°–75° C.

Preparative Example 3

4-Hydroxy-3-(3-hydroxypropyl)-1-(4-methoxyphenyl)-1,8-naphthyridin-2(1H)-one

A mixture of delta-valerolactone (120 ml.), ethyl 2-(4-methoxyphenylamino)nicotinate (12 g.) and potassium t-butoxide (24 g.) was stirred and heated in an atmosphere of nitrogen to 100° C. for 2 hrs. After cooling, the mixture was poured into 1000 ml. of 5% KOH solution and stirred overnight. The aqueous solution was extracted with ether (2×250 ml.) which was discarded. The aqueous solution was then acidified to pH 4.5 with conc. HCl. The product was filtered off, washed with water, dried in air and recrystallized from CHCl₃/isopropanol to yield the desired product, m.p. 229°–231° C.

According to this procedure, or an artrecognized modification thereof, any of the 3-hydroxypropyl sidechain materials used as starting materials in the reactions described in Examples 1-8 may be prepared.

Preparative Example 4

1-(3,4-Dichlorophenyl)-4-hydroxy-3-(2-hydroxypropyl)-1,8-naphthyridin-2(1H)-one

A stirred mixture of gamma-valerolactone (40 g.), ethyl 2-(3,4-dichlorophenylamino)-nicotinate (20 g.) and potassium t-butoxide (30 g.) was warmed in an atmosphere of nitrogen to 110° C. and kept there for 5 hr. After cooling somewhat the product was poured into 1000 ml. of 5% KOH solution and was allowed to stir overnight. The basic solution was extracted with ether (2×500 ml.) and the aqueous solution was acidified to pH 5 with conc. HCl. The solid was filtered off, washed with water, dried in air then recrystallized from methanol/charcoal to yield the desired product, m.p. 232°–234° C.

This procedure or an art-recognized modification thereof may be used to prepare any of the 2-hydroxypropyl side-chain starting materials for use in Examples 1–8.

Preparative Example 5

4-Hydroxy-3-(2-hydroxyhexyl)-1-phenyl-1,8-naphthyridin-2(1H)-one

A mixture of methyl 2-phenylaminonicotinate (5 g.), gamma-octanoic lactone (10 g.) and potassium t-butoxide (7.5 g.) was stirred in a nitrogen atmosphere and heated to 95° C. where it was held for 6 hrs. After cooling, the mixture was poured into 5% NaOH (200 ml.) and stirred overnight. Acidification to pH 4.6 yielded an oil, which was extracted with ether, washed with water, dried (Na$_2$SO$_4$), filtered, and evaporated to a small volume. Hexane was added until turbidity was noticed, and the mixture was allowed to stand for about 5 hrs. The solid was filtered off and recrystallized from CH$_2$Cl$_2$/isopropanol/isopropyl ether to produce the desired product, m.p. 184°–186° C.

This process, or an art-recognized modification thereof may be used to prepare any of the 2-hydroxyhexyl side-chain starting materials for use in Examples 1–8.

In general, by following the procedures described in Preparative Examples 1, 4, 5 or 6, or an art-recognized modification thereof, using lactones with desired substituents, other intermediates, II (B=O), useful for conversion to the products of the invention according to one of the methods described in Examples 1–8 and 10 may be prepared.

We claim:

1. A method for increasing cardiac contractility in a mammal which method comprises administering to said mammal a positive inotropic effective amount of a compound having the structural formula I

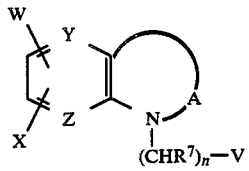

wherein:

A is

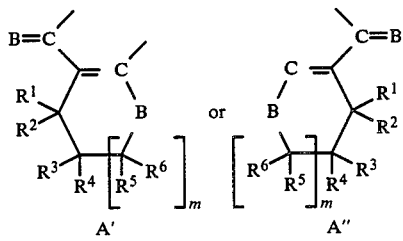

B is independently oxygen or sulfur;
R$^1$–R$^6$ may be the same or different and are hydrogen or alkyl having from 1 to 6 carbon atoms;

m is 0 or 1, provided that, when m is 0, R$^2$ and R$^4$ may be joined to form a carbon to carbon bond;

n is 0, 1 or 2;

W and X may be the same or different and are hydrogen, alkyl having from 1 to 6 carbon atoms, alkoxy having from 1 to 6 carbon atoms, halogen, trifluromethyl, nitro, cyano, carboxy, hydroxy, alkenyloxy having from 3 to 8 carbon atoms, alkynyloxy having from 3 to 8 carbon atoms, cycloalkyl having from 4 to 8 carbon atoms, S(O)$_p$R$^a$ wherein p is 0, 1 or 2 and R$^a$ is alkyl having from 1 to 6 carbon atoms, or phenoxy wherein the benzene ring may be substituted with any of the other substituents W and X;

Y and Z may be the same or different and are CH or N;

V is phenyl, naphthyl, idenyl, indanyl, pyridyl, pyrimidinyl, thienyl, furyl or thiazolyl, any of which may be substituted with W and X as defined herein; and R$^7$ is independently hydrogen or alkyl having from 1 to 6 carbon atoms.

2. The method defined in claim 1 wherein n is 0.

3. The method defined in claim 2 wherein Y is CH.

4. The method defined in claim 3 wherein the compounds have the structural formula:

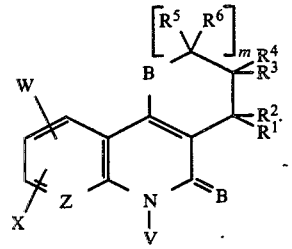

5. The method defined in claim 4 wherein Z is N.

6. The method defined in claim 5 wherein m is 0.

7. The method defined in claim 6 wherein the compounds have the structural formula:

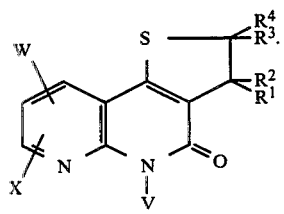

8. The method defined in claim 6 wherein the compounds have the structural formula:

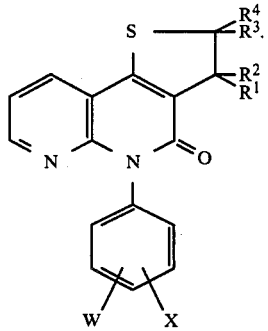

9. The method defined in claim 8 wherein W is 3-chloro and X is hydrogen, chlorine or fluorine.

10. The method defined in claim 8 wherein W is 3-methoxy and X is hydrogen or fluorine.

11. The method defined in claim 8 wherein W and X are both hydrogen.

12. The method defined in claim 6 wherein B is oxygen.

13. The method defined in claim 12 wherein V is

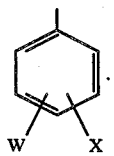

14. The method defined in claim 13 wherein the compounds have the structural formula:

15. The method defined in claim 14 wherein $R^1$-$R^4$ are hydrogen or methyl.

16. The method defined in claim 15 wherein zero or one of $R^1$-$R^4$ is methyl and the rest are hydrogen.

17. The method defined in claim 16 wherein W is 3-chloro and X is hydrogen, chlorine or fluorine.

18. The method defined in claim 16 wherein W is 3-methoxy and X is hydrogen or fluorine.

19. The method defined in claim 16 wherein W and X are both hydrogen.

20. The method defined in claim 1 which utilizes the compounds having the following names:
3,5-dihydro-5-phenyl-furo[3,2-c][1,8]naphthyridin-4[2H]-one;
6-phenyl-2,3,4,6-tetrahydro-pyrano[3,2-c][1,8]naphthyridin-5-one;
2-methyl-3,5-dihydro-5-phenyl-furo[3,2-c][1,8]naphthyridin-4[2H]-one;
3,9-dihydro-9-phenyl-furo[2,3-b][1,8]naphthyridin-4[2H]-one;
3,9-dihydro-9-(4-methylphenyl)-furo[2,3-b][1,8]naphthyridin-4[2H]-one;
3,9-dihydro-2-methyl-9-phenyl-furo[2,3-b][1,8]naphthyridin-4[2H]-one;
3,5-dihydro-5-(p-methylphenyl)-furo[3,2-c][1,8]naphthyridin-4[2H]-one;
3,5-dihydro-5-(p-fluorophenyl)[furo[3,2-c][1,8]naphthyridin-4[2H]-one;
3,5-dihydro-5-(m-methoxyphenyl)-furo[3,2-c][1,8]naphthyridin-4[2H]-one;
3,5-dihydro-5-(m-methylthiophenyl)-furo[3,2-c][1,8]naphthyridin-4[2H]-one;
3,9-dihydro-9-(p-fluorophenyl)-furo[2,3-b][1,8]naphthyridin-4[2H]-one;
3,9-dihydro-9-(m-methoxyphenyl)-furo[2,3-b][1,8]naphthyridin-4[2H]-one; and
3,9-dihydro-9-(m-methylthiophenyl)-furo[3,2-c][1,8]naphthyridin-4[2H]-one.

21. A pharmaceutical composition useful for producing an increase in cardiac contractility in a mammal which comprises a compound having structural formula I as defined in claim 1, in combination with a pharmaceutically acceptable carrier.

* * * * *